United States Patent [19]

Klenner et al.

[11] Patent Number: 4,757,016

[45] Date of Patent: Jul. 12, 1988

[54] PROCESS FOR STABILIZING THE ACTIVITY OF PEROXIDASE IN SOLUTION

[75] Inventors: Dagmar Klenner; Gerd Kleinhammer, both of Tutzing; Rolf Deeg, Bernried, all of Fed. Rep. of Germany

[73] Assignee: Boehringer Mannheim GmbH, Mannheim-Waldhof, Fed. Rep. of Germany

[21] Appl. No.: 835,896

[22] Filed: Mar. 4, 1986

[30] Foreign Application Priority Data

Mar. 28, 1985 [DE] Fed. Rep. of Germany ....... 3511327

[51] Int. Cl.$^4$ .......................... C12N 9/96; C12N 9/08; C12Q 1/28
[52] U.S. Cl. ..................................... 435/188; 435/28; 435/192
[58] Field of Search .......................... 435/192, 188, 28

[56] References Cited

U.S. PATENT DOCUMENTS

| 4,252,896 | 2/1981 | Shaffar | 435/7 |
| 4,331,761 | 5/1982 | Dawson et al. | 435/188 |
| 4,350,762 | 9/1982 | DeLucia et al. | 435/10 |
| 4,378,429 | 3/1983 | Modrovich | 435/11 |
| 4,504,579 | 3/1985 | Sun | 435/28 |

FOREIGN PATENT DOCUMENTS 0024578 3/1981 European Pat. Off. .
0070992 2/1983 European Pat. Off. .

Primary Examiner—Lionel M. Shapiro
Attorney, Agent, or Firm—Felfe & Lynch

[57] ABSTRACT

The present invention provides a process for stabilizing the activity of peroxidase in solution by the addition of a specific activity stabilizer, wherein, to the enzyme present in solid or dissolved form, when the peroxidase is used as a conjugate with an immunologically effective substance, there is added, as activity stabilizer, aminopyrine in an amount of from 0.0005 to 2% by weight, referred to the solution.

12 Claims, No Drawings

PROCESS FOR STABILIZING THE ACTIVITY OF PEROXIDASE IN SOLUTION

The present invention is concerned with a process for stabilising the activity of peroxidase in solution.

Peroxidase is a widely used enzyme, especially for enzymatic detection reactions. Peroxidase has also found wide use as a labelling enzyme for the numerous forms of enzyme immune tests (EIA). Peroxidases of various origins and especially horseradish peroxidase can be detected quickly and quantitatively by a number of methods.

Upon this is based the very good suitability of peroxidase as a detection and labelling enzyme. On the other hand, however, peroxidase suffers from the disadvantage that it does not have a completely satisfactory stability, especially in comparatively high dilution and in solution. Therefore, the period of life of especially peroxidase conjugates in enzymatic test reagents or in other enzyme preparations is limited and a stabilization is necessary in order to achieve the desired storage stability.

It is already known from Federal Republic of Germany Patent Specification No. 31 00 076 to stabilise peroxidase in a medium containing serum protein by the addition of 8-anilino-1-naphthalenesulphonic acid (ANS). From European Patent Specification No. 0,070,992, it is known to use 4-aminoantipyrine for the stabilization of peroxidase in a serum or in a medium containing serum protein. Finally, from U.S. Pat. No. 4,169,012, it is known to stabilize peroxidase by means of polyvalent ions of Groups III and IV of the Periodic System, for example aluminium, zinc, magnesium, iron and copper. However, these known activity stabilizers have a poor compatibility with other components of conventional reagent combinations or still leave something to be desired with regard to the activity stabilization. Furthermore, they sometimes have a negative influence on immune reactions when the peroxidase is present as a conjugate with an immunologically-active substance, which results in very flat calibration curves.

Therefore, it is an object of the present invention to stabilize the activity of peroxidase or of peroxidase conjugates in solution without the abovementioned disadvantages and without a disadvantageous influencing of the actual immune reaction.

Thus, according to the present invention, there is provided a process for stabilizing the activity of peroxidase in solution by the addition of a specific activity stabilizer, wherein, to the enzyme present in solid or dissolved form, there is added, as activity stabilizer, aminopyrine in an amount of from 0.0005 to 2% by weight, referred to the solution.

According to the present invention, the enzyme activity of free peroxidase or of peroxidase possibly also present covalently bound in a conjugate is stabilized against the inactivating influence of temperature, foreign substances and the like, which is especially marked in dilute solutions. This means that the rapid decrease of enzyme activity occurring in solution is overcome or considerably reduced without the immunological effectiveness of an immunologically-active substance in the conjugate bound to the peroxidase being impaired.

As already mentioned, the activity stabilizer used according to the present invention is added in an amount of from 0.0005 to 2% by weight, referred to the volume of the solution in which the peroxidase is contained. In the case of exceeding the upper limit of 2% by weight, the stressability with regard to the action of heat is admittedly maintained as before but the peroxidase activity itself is again reduced. Below the lower limit, a satisfactory stabilization can no longer be achieved. The activity stabilizer used according to the present invention is preferably added in an amount of from 0.005 to 1.0% by weight.

The activity stabilizer can be added at any desired point of time to the enzyme or enzyme conjugate present in solid or dissolved form. It is preferred to make the addition to a solution since a more uniform distribution of the stabilizer is thereby achieved and thus a better action even in the case of additions close to the lower limit of the effective range. In particular, the aminopyrine can be added to the enzyme or conjugate solution before lyophilization or after reconstitution of a lyophilizate with an aqueous solvent. In the latter case, of course, the solvent can first be mixed with the activity stabilizer and then added to the lyophilizate for dissolving it.

As immumologically-effective substance in a conjugate, there is preferably used an antibody or a fragment thereof, an antigen or a hapten.

As antigens or haptens, there can be used, for example, proteins, drugs, steroids and hormones, examples thereof including TBG, cortisol, vitamin B12, digoxin, digoxigenin and thyroxine.

As antibodies, there can be used polyclonal and monoclonal antibodies and fragments thereof. There can also be used chemically modified derivatives thereof, for example antibodies cross-linked with glutardialdehyde, as components of the conjugate. Examples thereof include antibodies against TSH, hCG, AFP, LH, FSH, prolactin, ferritin, CEA and insulin.

As peroxidase, there can be used all types of this enzyme but, because of its ready availability, horseradish peroxidase is preferred.

In the case of the process according to the present invention, in addition to the mentioned activity stabilizer, a preserving agent is preferably also added. Appropriate preserving agents include, for example, merthiolate, Germall, Dowicil and Kathon CG.

The present invention also provides a stabilized enzyme preparation with a content of peroxidase or of a peroxidase conjugate, wherein it contains 0.0005 to 2% by weight of aminopyrine.

With regard to the components of the conjugate, the amounts of the activity stabilizer and a possible content of an additional preserving agent, the remarks made hereinbefore with regard to the process apply equally to the stabilized enzyme preparation. Furthermore, the enzyme preparation preferably also contains a buffer substance, for example phosphate, citrate or borate buffer or the like, and/or bovine serum albumin and/or a system for the detection of peroxidase activity.

The present invention makes possible a stabilisation of the enzyme activity of peroxidase and of peroxidase conjugates against the rapid decrease of activity which normally occurs in solution without disadvantageously influencing the immune reaction in the case of conjugates. According to the present invention, the activity stabilization thereby also takes place even in the case of higher temperatures over a long period of time so that the usability of solutions ready for use of peroxidase and peroxidase conjugates is substantially improved.

The following Examples are given for the purpose of illustrating the present invention:

EXAMPLE 1

Stabilization of antibody-peroxidase conjugate

| Solution 1 - incubation buffer: | |
| --- | --- |
| phosphate buffer (pH 7.4) | 40 mmol/l. |
| bovine Ig | 0.1% by weight |
| merthiolate | 0.01% by weight |
| Solution 2: | |
| Anti-ferritin-peroxidase conjugate dissolved in Solution 1 | about 10 U/l. |
| Solution 3 - substrate/buffer solution: | |
| phosphate-citrate buffer (pH 4.4) | 100 mmol/l. |
| sodium perborate | 3.2 mmol/l. |
| 2,2'-azino-di-(3-ethyl-benzthiazoline-6-sulphonic acid) diammonium salt | 1.9 mmol/l. |

The solutions used, coated test tubes and standards originate from the ferritin Enzymun test of Boehringer Mannheim GmbH (order No. 677 337). The carrying out of the determination takes place according to the manufacturer's instructions.

Into test tubes coated with anti-ferritin antibodies are placed 1 ml. of Solution 1 and 0.1 ml. ferritin standard (about 440 ng./ml.) and incubated for 60 minutes at 20° to 25° C. After sucking out and rinsing, 1 ml. of Solution 2 is added thereto. The Solution 2 used herefor is either freshly made (comparative measurement) or, before addition, is incubated for 24 hours at 30° C., in which case 0.02% by weight of aminopyrine are possibly added thereto.

After incubation for 60 minutes at 20° to 25° C., the test tubes are sucked out and rinsed. Subsequently, 1 ml. of Solution 3 is added thereto and incubation further carried out for 60 minutes at 20° to 25° C. Thereafter, against Solution 3 as blank, there is carried out a photometric determination at $\lambda = 405$ nm.

The values set out in the following Table 1 are, in each case, referred to the relative value of 100% which was obtained with a test in which was used freshly prepared Solution 2 (without aminopyrine). Analogous measurements are carried out with:

| Enzymun test ferritin | Order No. 67 73 37 |
| --- | --- |
| Enzymun test TBK | Order No. 24 94 16 |
| Enzymun test AFP | Order No. 71 14 11 |
| (producer: Boehringer Mannheim GmbH). | |

TABLE 1

| | 0 hours | | 24 hours | |
| --- | --- | --- | --- | --- |
| aminopyrine 0.02% by wt. | + | − | + | − |
| POD conjugate: | activity | | activity | |
| anti-ferritin-POD | 100% | 100% | 90% | 48% |
| anti-AFP-POD | 100% | 100% | 94% | 70% |
| T₄-POD (TBK test) | 100% | 100% | 94% | 11% |

EXAMPLE 2

Measurements with the Enzymun test ferritin are carried out, in a manner analogous to that described in Example 1, with different antipyrine concentrations. The results obtained are given in the following Table 2:

TABLE 2

| aminopyrine concentration | activity after stressing for | |
| --- | --- | --- |
| | 0 hours at 30° C. | 24 hours at 30° C. |
| none | 100% | 50% |
| 0.005% | 100% | 90% |
| 0.02% | 100% | 90% |
| 0.05% | 100% | 91% |
| 0.1% | 100% | 86% |
| 0.4% | 100% | 83% |
| 1% | 100% | 101% |

We claim:

1. A process for stabilizing the activity of peroxidase enzyme in solution wherein the peroxidase is used as a conjugate with an immunologically effective substance by the addition of a specific stabilizer comprising adding to the enzyme in solid or dissolved form as the activity stabilizer, aminopyrine in an amount of from 0.0005 to 2% by weight, referred to the solution.

2. The process of claim 1, wherein 0.005 to 1% by weight of aminopyrine are added.

3. The process of claim 1 further comprising, after the aminopyrine is added, lyophilizing the enzyme solution.

4. The process of claim 1, wherein the enzyme is in the form of a lyophilizate which has been reconstituted in aqueous solvent and the aminopyrine is added to the reconstituted lyophilisate.

5. The process of claim 1, wherein the immunologically-effective substance is an antibody or a fragment thereof, an antigen or a hapten.

6. The process of claim 5, wherein the immunologically-effective substance is digoxin, digoxigenin, or thyroxin or an antibody against TSH, ferritin or AFP.

7. The process of claim 5, wherein the immunologically-effective substance is an antibody against AFP, ferritin or TSH.

8. The process of claim 1 further comprising adding a preserving agent.

9. A composition comprising a stabilized peroxidase enzyme preparation wherein the peroxidase is conjugated with an immunologically effective substance peroxidase together with 0.005 to 2% by weight of amino pyrine.

10. The process of claim 5 wherein the immunologically-effective substance is TBG, cortisol, vitamin B12, or an antibody against hCG, LH, FSH, prolactin, CEA or insulin.

11. The stabilized peroxidase enzyme preparation of claim 9 wherein 0.005 to 1% by weight of aminopyrine is used.

12. The stabilized peroxidase enzyme preparation of claim 11 wherein the immunologically-effective substance is an antibody or fragment thereof, an antigen or a hapten.

* * * * *